United States Patent [19]

Hüschelrath

[11] Patent Number: 4,727,321
[45] Date of Patent: Feb. 23, 1988

[54] METHOD AND DEVICE FOR MAGNETIC AND ULTRASONIC TESTING OF FERRO-MAGNETIC OBJECTS

[75] Inventor: Gerhard Hüschelrath, Laufach-Frohnhofen, Fed. Rep. of Germany

[73] Assignee: Nukem GmbH, Hanau, Fed. Rep. of Germany

[21] Appl. No.: 858,726

[22] Filed: May 2, 1986

[30] Foreign Application Priority Data

May 3, 1985 [DE] Fed. Rep. of Germany ....... 3515977

[51] Int. Cl.⁴ .................... G01N 27/83; G01N 29/04; G01R 33/12
[52] U.S. Cl. ...................... 324/226; 73/601; 73/643; 324/228; 324/235
[58] Field of Search .............. 324/226, 227, 228, 232, 324/235, 262; 73/601, 643

[56] References Cited

U.S. PATENT DOCUMENTS

| | | | |
|---|---|---|---|
| 3,237,446 | 3/1966 | Wood | 324/226 X |
| 3,460,063 | 8/1969 | Houck et al. | 73/643 X |
| 3,850,028 | 11/1974 | Thompson et al. | 324/232 X |
| 4,309,905 | 1/1982 | Maizenberg et al. | 324/227 X |
| 4,418,574 | 12/1983 | Flournoy | 324/226 X |
| 4,449,408 | 5/1984 | Brooks et al. | 324/226 X |
| 4,449,411 | 5/1984 | Suhr et al. | 324/227 X |
| 4,538,108 | 8/1985 | Huschelrath et al. | 324/232 |

FOREIGN PATENT DOCUMENTS 0208451 12/1982 Japan ................... 324/226

OTHER PUBLICATIONS

Shubaev, S. N. Analysis of the Acoustic Field Excited by an Electromagnetic Field; Soviet Journal Nondestructive Testing (USA) vol. 10, No. 3, May–Jun. 1974, pp. 306–334.

Primary Examiner—Gerard R. Strecker
Attorney, Agent, or Firm—Cushman, Darby & Cushman

[57] ABSTRACT

The subject of the invention is a method and a device for non-destructive testing of ferromagnetic bodies (1) for structural faults. The bodies (1) are magnetized. Structural faults cause changes in the magnetic field pattern which are measured with magnetic field detectors (6). Surface waves are generated electro-dynamically utilizing the magnetic field generated for magnetizing the body (1). Those structural faults extending up to the surface can be detected with the surface waves. To distinguish between the structural faults extending to the surface of the body at one point and those structural faults inside the body (1), it is determined whether the measured values gained both from the leakage flux and from the surface waves indicate structural faults or whether only the measured values gained from the leakage flux indicate structural faults.

17 Claims, 7 Drawing Figures

METHOD AND DEVICE FOR MAGNETIC AND ULTRASONIC TESTING OF FERRO-MAGNETIC OBJECTS

The invention relates to a method for non-destructive testing of ferromagnetic bodies for structural faults by means of magnetizing the bodies in which the structural faults cause in the magnetic field pattern changes, which are measured by magnetic field detectors, and to a device for implementation of the method.

Detection of faults in ferromagnetic bodies using the "leakage flux method" is known. Structural faults in the bodies cause leakage fluxes outside those surface areas on or under which the structural faults are located. The leakage fluxes are measured with magnetic field detectors on or near the surfaces of the bodies and attached stationary or rotating around the body.

It is not possible with the leakage flux method to ascertain with certainty whether the structural faults extend to the surface of the body, i.e. are external faults, or not, i.e. are internal faults.

The object underlying the invention is to further develop a method of the type described at the outset to the effect that a distinction can be made without major expense between external and internal faults.

In attaining this object and other objects, the invention provides for magnetizing the respective body in which structural anomalies cause changes in the magnetic field pattern, thereby generating leakage flux which is measured by magnetic field detectors and generating from a common source of magnetic field electrodynamically ultrasonic surface waves, being used to measure structural anomalies extending to the surface of the body. To distinguish between structural anomalies reaching the surface at one point, respectively, and structural anomalies not reaching the surface, a check is made to determine whether measured values gained both from the leakage flux and from ultrasonic surface waves indicate structural anomalies, or whether measured values gained from the leakage flux only indicate structural anomalies. The size and/or form of the anomalies measured by the leakage flux are evaluated to determine the depth of penetration of a structural anomaly when a structural anomaly is detected, which extends to the surface of the respective body. Internal and external faults have different effects when the body is subjected to stresses. Knowledge of the nature of the faults is therefore important for deciding whether the respective body meets its specifications or not. Some faults, for example external faults, can be remedied by reworking.

Preferably, the size and/or form of the leakage flux measured value is evaluated when an external fault is detected, in order to ascertain the depth of penetration of the said external fault. If a structural fault is recognized as being external, then the depth of the fault is determined too. Once the depth of penetration of an external fault is known, it is easier to decide whether and how reworking can remedy the fault.

In a long body magnetized in the transverse direction and where a relative movement between the body and the testing/measuring system takes place during testing, it is appropriate to generate Rayleigh waves to determine structural faults extending longitudinally along the body, while shear waves acoustically irradiated in glancing manner detect structural faults which extend in the transverse direction of the body.

The type of wave excited and its direction of propagation depend on the position of the current conductors of the transmitting coil in relation to the direction of the overlaid magnetic field. If the external overlaid magnetic field runs parallel to the current conductors, a shear wave is excited. The current-carrying conductors are, like the external magnetic field, arranged transverse to a body being tested in order to generate shear waves in the longitudinal direction, to detect anomalies in the longitudinal direction. If the external overlaid magnetic field runs vertical to the current-carrying conductors, a Rayleigh wave is caused. The magnetic field must be arranged transverse to the body being tested and the current conductors longitudinal to said body, in order to generate Rayleigh waves that run transverse to the body being tested. This permits faults in the longitudinal direction of the body to be detected.

The method set forth above is used mainly to test pipes, rod, strips and similar.

A device in accordance with the invention includes at least two magnetic poles of magnets aligned with the body being tested, and at least one magnetic field detector arranged close to the surface of the body in the space between the magnetic poles and an electrodynamic transducer of ultrasonic surface waves having at least one transmitting coil is arranged at a point close to the surface of the body at which the magnetic field has both field lines entering the body from the outside and field lines running in the direction of the surface parallel thereto. The electro-dynamic transducer is preferably located close to a magnetic pole. A magnetic field line pattern develops in the vicinity of the magnetic pole that is particularly favourable to the generation of Rayleigh waves. Leakage field lines entering the body outside the pole surface projected onto the surface of the body result in a field component running vertical to the surface. The body however already contains a field component whose field lines follow the contour of the surface of the body at varying distances to the surface. Thanks to the above positioning of the transducer close to the surface of the body at one of the magnetic poles, both variously aligned magnetic field components can be utilized, when the conductor of the transducer is oriented in the longitudinal direction of the respective body, to generate a Rayleigh wave extending in the transverse direction, whereby the efficiency of the transducer is increased. When the conductor of the transducer is oriented in the transverse direction, the magnetic filed component in the transverse direction can be utilized to generate a shear wave extending in the longitudinal direction. It is thereby possible with the magnetization described to generate surface waves extending in various directions. This permits structural faults to be detected that differ in their directions. Depending on the required strength of the various magnetic field components at the position of the transmitting coil for electro-dynamically generated surface waves, it is possible to vary the size of the distance between the pole surface of the magnetic pole. The leakage flux proportion increases with greater distances, i.e. the component aligned vertically to the body surface at the position of the transmitter becomes stronger.

In a preferred embodiment, the electro-dynamic transducer has a receiving coil linked to a threshold value detector by a logic circuit to which the magnetic field detector is connected via a signal processing array, with the said logic circuit being connected to an error register whose stored values from the logic circuit or signal processing circuit can be input synchronously with the testing clock pulses generated in the transmitting coil of the electrodynamic transducer. Using the testing clock pulses, which are each related to surface areas which can be determined for example with the aid of position sensors, it is therefore possible to pinpoint faults to those points on the surface on or under which there are structural faults. The logic circuit ascertains whether both the received electro-dynamic signal and the leakage flux signal have exceeded the threshold specified as fault indicator. If this is the case, the logic circuit gives an appropriate signal to the error register. The appropriate stored value identifies an external fault. If however only a leakage flux signal exceeding the respective threshold value is present, then an appropriate value is input into the error register. This value then indicates that the fault is internal.

In another preferred embodiment, the electrodynamic transducer has a meander-wound transmitting coil whose turns are arranged in grooves of a coil spool arranged at a constant distance from the surface of the body. Both Rayleigh and shear waves can be generated with a device of this nature.

The receiving coil is preferably designed meander-shaped and arranged interlaced with the transmitting coil in the grooves of the spool. This permits a reduction in the dimensions of the spool.

It is appropriate to connect a series capacitance to the transmitting coil or a parallel capacitance to the receiving coil, and to design the arrangement comprising the transmitting winding and the series capacitance or the receiving coil and the parallel capacitance as a resonant circuit. This permits an increase in the efficiency of the conversion of electrical to acoustic energy and of acoustic to electrical energy.

The transmitting coil is preferably provided with numerous turns, which are connected by groups in parallel to a testing pulse generator designed as a transistor transmitter. The transmitting coil together with the body are a transformer. The above mentioned arrangement achieves high resistances transferred to the primary to match the internal resistance of the transistor transmitter.

It is favourable to select a number of turns for the receiving coil large enough for the internal capacitance to determine a cut-off frequency somewhat greater than the frequency of the testing clock pulses. The cut-off frequency corresponds to the resonant frequency of the receiving coil. The frequency of the testing clock pulses or burst pulses is below the resonant frequency. This also permits an improvement in conversion efficiency.

In another useful embodiment, a second transmitting coil is arranged interlaced in the first transmitting coil, with the two transmitting coils receiving 90° phase-shifted testing clock pulses. In an arrangement of this type, surface waves are predominantly only radiated in one direction.

The magnets, the magnetic field detector, and the transmitting and receiving coils together with the spool are preferably arranged stationary, while the body being tested carries out a rotary movement and a longitudinal shift movement. It is however also advantageous to design the magnets, the magnetic field detector, and the transmitting and receiving coils rotatable around the longitudinal axis of the body being tested and to shift the body in its longitudinal direction during testing.

In the following, the invention is described using embodiments shown in the drawing, indicating further features and advantages.

Figure 1:
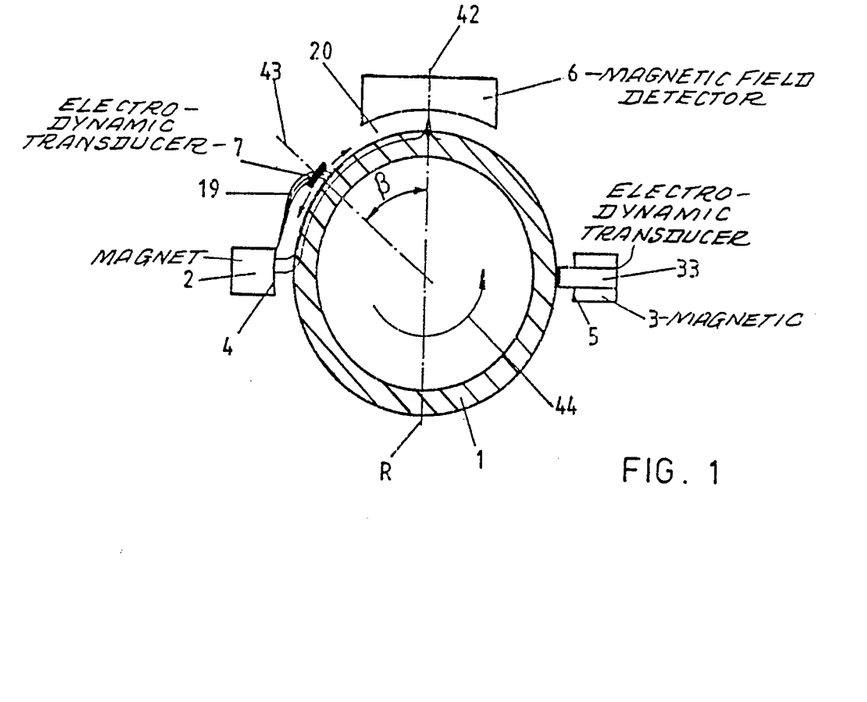
FIG. 1 shows a cross-section through a device for testing ferromagnetic bodies using the leakage flux method and with surface waves.

A ferromagnetic body for non-destructive testing for structural faults is a pipe 1 which is moved in the longitudinal direction and rotated at the same time through a testing station during testing. It is however also possible to design the testing station rotatable about a longitudinal axis with the test body being moved in the longitudinal direction but not performing a rotary movement during testing. Instead, the testing station rotates around the body. In addition, the test body can be stationary, while the testing station is turned and moved in the longitudinal direction. The testing station has a magnetization system having at least one pair of magnets 2, 3, which are connected by a yoke not illustrated. Magnets 2, 3 contain pole shoes 4, 5, arranged on diametrically opposed sides of pipe 1 at identical distances from the surface of the pipe. Magnets 2, 3 generate such a strong magnetic field that the pipe walls are magnetically saturated. Cracks, shrinkage cavities or holes in the walls of pipe 1 greatly increase the magnetic resistance at the points in question. Part of the magnetic field does not close over the respective structural fault, but over the air gap outside the external or internal pipe surface as the case may be. The part running outside the external surface of the pipe 1 is picked up by at least one magnetic field detector 6 arranged a short distance from the outer surface of the pipe 1 approximately in the middle between the two magnets 2, 3. A Hall generator is used, for example, as magnetic field detector. Several magnetic field detectors can also be arranged at the same distances from the pipe surface in a row symmetrical to the pole shoes 4, 5. If a wall section of pipe 1 in which there is a structural fault moves past magnetic field detector 6, the magnetic leakage flux caused by the structural fault generates a voltage in magnetic field detector 6. This voltage is a dimension for the structural fault. A structural fault is therefore a fault in the pipe. Faults of this type can extend parallel to the longitudinal axis, transverse to the longitudinal axis or inclined at an angle to the longitudinal axis of pipe 1. To detect both longitudinal and transverse faults, the magnetic field detector is best arranged inclined at an angle to the longitudinal axis of pipe 1. In addition to the measurement of the magnetic leakage flux to detect errors in pipe 1 due to structural faults, a further fault detecting operation is carried out with the aid of surface waves generated electro-dynamically on the outside of pipe 1. To generate surface waves, an electro-dynamic transducer 7 described in detail below is arranged between magnet 2 and magnetic field detector 6 on or near to the surface of pipe 1. The electro-dynamic transducer 7 generates in pipe 1 ultrasonic waves which propagate along the surface.

The principle of electro-magnetic ultrasonic excitation in conductive materials is based on the generation of dynamically mechanical forces in the surface of the material when a quasi-static magnetic field and an electro-magnetic high frequency field are superimposed. One coil for generation and one coil for reception of the electromagnetic alternating field are the actual transducer.

Figure 2:
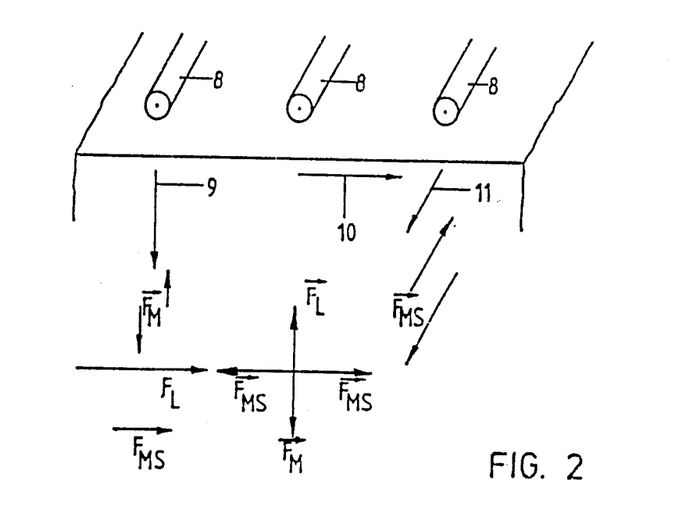
FIG. 2 shows a section of a body to be tested, with conductors arranged outside the body and in which current pulses are generated.

FIG. 2 is a diagram of the various physical mechanisms of electro-magnetic ultrasonic excitation which can occur in the various orientations of conductors 8 and external magnetic field. Three vectors 9, 10, 11 pointing in various directions are shown in FIG. 2. These vectors indicate the direction of the externally generated magnetic field. The Lorentz force and magentic forces affect the currents induced in pipe 1. Magnetostrictive forces also occur. Underneath vectors 9, 10, 11, vectors $F_M$, $F_L$, $F_{MS}$ are illustrated, indicating the directions of the magnetic forces, the Lorentz force and the magnetostrictive forces.

Various types of surface wave occur under the influence of the above forces, a longitudinal creep wave (Kriechwelle), a shear wave acoustically irradiated in grazing manner, and a Rayleigh wave. The position of the electro-dynamic transducer 7 between the magnet 2 and the magnetic field detector 6 is so selected that magnetic field components are present in the surface section under the transducer that have the directions of vectors 9 and 11. Magnetic field components with the directions of vectors 9 and 11 result at points at which field lines run concentrically in the wall of pipe 1 and leakage fluxes are emitted from magnet 2 in addition. These leakage fluxes cause the magnetic field components aligned vertical to the surface of pipe 1. Preferably, a Rayleigh wave is used for determining a longitudinal fault in pipe 1, and a shear wave acoustically irradiated in grazing manner for determining a transverse fault. To excite Rayleigh waves, the magnetic field components must run in the direction of vectors 10 or 9 in the direction of the conductors 8 shown in FIG. 2. Shear waves are excited with the conductors 8 if the magnetic field components run in the direction of vector 11.

A Rayleigh wave is a guided, transverse-damped wave with intensity diminishing exponentially with depth, and which can be excited both by forces vertical to the surface and in the propagation direction parallel to the surface. The distribution of intensity of a shear wave is determined by the directional characteristic of the transducer. As a result of its oscillation direction parallel to the surface, it can be excited by forces parallel to the surface and vertical to the direction of propagation.

In view of the magnetic field conditions prevailing at the location (field lines both vertical and parallel to the surface in the circumferential direction), it is possible, when the conductor of the coil of the electro-dynamic transducer 7 is oriented to the longitudinal direction of the pipe 1, that all three conversion mechanisms are excited and that the forces necessary to generate a Rayleigh wave travelling in the circumferential direction are transmitted to the surface. When the conductors are oriented in the circumferntial direction, conductor and external magnetic field are parallel to one another, and a shear wave expanding in the longitudinal direction of the pipe can be excited.

Figure 3:
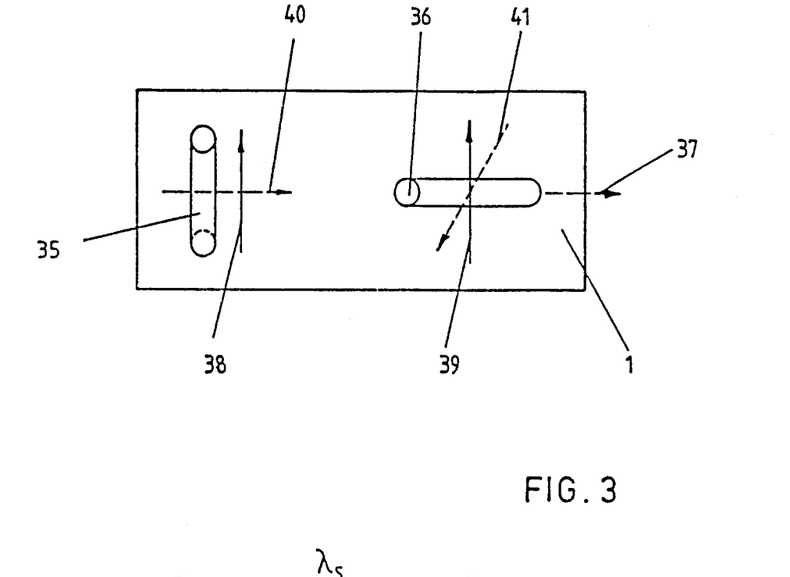
FIG. 3 shows a diagrammatic view of an arrangement of current-carrying conductors based on the direction of external magnetic fields and on the dimensions of the body shown in side view for generating Rayleigh waves or shear waves.

FIG. 3 is a side view of pipe 1. Two conductors 35 and 36 are arranged vertical and parallel respectively to the longitudinal axis 37 of pipe 1 close to its surface. A first magnetic field, illustrated in FIG. 3 by vector 38, runs mainly parallel to conductor 35. A second magnetic field, shown in FIG. 3 by a vector 39, has the same direction as the first magnetic field and runs vertical to conductor 36. A shear wave can be generated with conductor 35 whose vector is numbered 40 in FIG. 3. This shear wave travels in the longitudinal direction of pipe 1. A Rayleigh wave can be generated with conductor 36 whose vector is numbered 41 in FIG. 3. The Rayleigh wave travels in the transverse direction of pipe 1. To generate Rayleigh waves, the magnetic field can also run vertical to the drawing plane in relation to conductor 36. Between wavelengths $\lambda_s$ of the shear wave, transversal wave velocity $C_t$ and frequency f, the relationship is $$f = C_t/\lambda_s$$

For the Rayleigh wave, the relationship is: $f = C_R/\lambda_s$, where $C_R$ is the propagation velocity of the Rayleigh wave.

The excited wave type and its direction of propagation are accordingly determined by the position of the respective current-carrying conductor of the transmitting coil in relation to the direction of the externally overlaid magnetic field and by the frequency or trace wave (Spurwelle) length of transducer 7.

Figure 4:
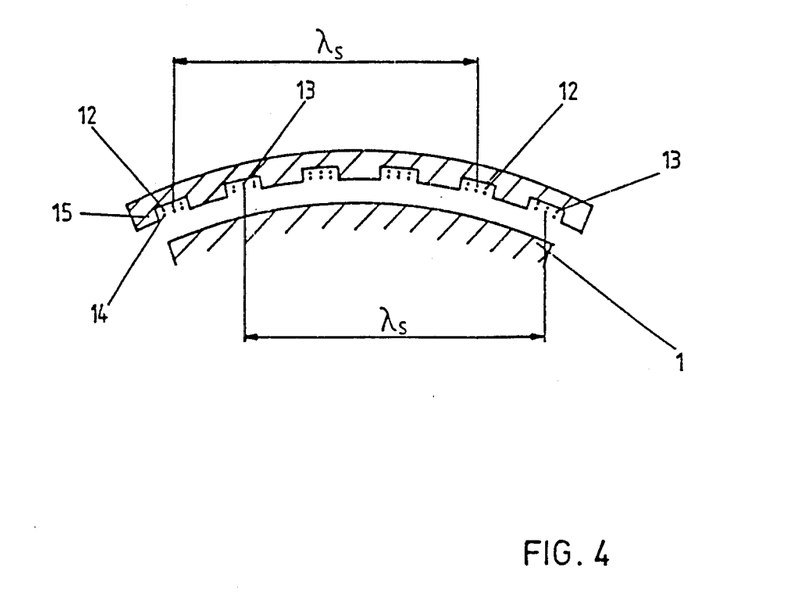
FIG. 4 shows a cross-section through a spool with turns of a transmitting and a receiving coil arranged in grooves, using which spool Rayleigh or shear waves can be generated depending on the position of the turns in relation to the body to be tested.
Figure 5:
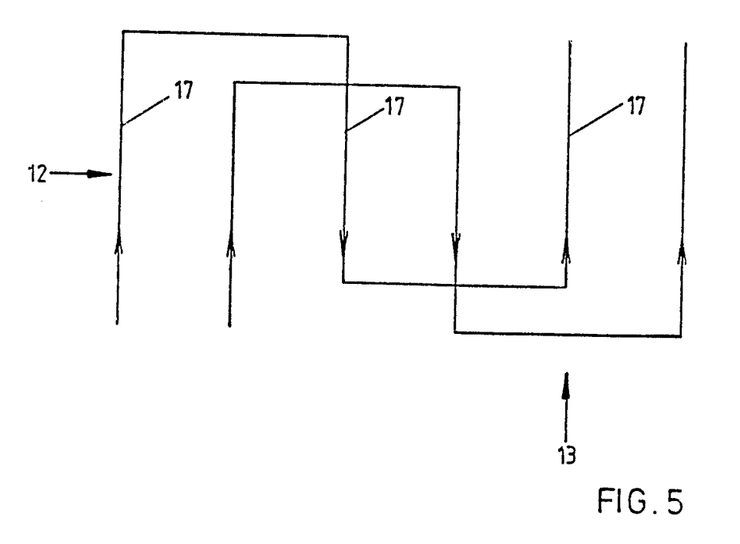
FIG. 5 shows a diagram of the winding in a transmitting and a receiving coil.

FIG. 4 shows the arrangement of the electro-dynamic transducer 7. It has a transmitting and a receiving coil, 12 and 13, whose turns are arranged in grooves 14 of a spool 15 of thin plastic. The transmitting coil 12 and the receiving coil 13 are each wound in a meandering manner. The distance between two conductors of a winding forming an arc is half the length of the sound wave $\lambda_s$, i.e. the conductors are located in grooves 14 arranged parallel to one another and spaced half the ultrasonic wave length apart. The coils are composed of several rectangular windings arranged next to one another. In FIG. 4, this is illustrated by several conductors represented by dots in the grooves 14. The spool 15 arches slightly above the outer surface of pipe 1. The distance between pipe 1 and the spool 15 is constant. The transmitting and the receiving coils are interlaced to achieve a smaller aperture. Grooves 14 with transmitting coil conductors and grooves 14 with receiving coil conductor alternate with a spacing of ¼ of the ultrasonic wave length.

The number of turns per winding and the wire thickness depend on the required impedances. On the conductive body 1, the transmitting coil functions as a transformer with the coil itself as the primary side and the test body as the secondary side.

To improve the efficiency of the electro-dynamic transducer 7, the transmitting and receiving circuits are best designed as resonant circuits by arranging a series capacitance, not illustrated further, in the transmitting circuit or a parallel capacitance, not illustrated further, in the receiving circuit. The respective circuit is then operated with its resonant frequency.

The transmitting coil is best provided with numerous turns in order to achieve high resistance transferred to the primary. The number of turns and the wire thickness must be matched here to achieve high resistances. A transistor transmitter is preferably used as pulse generator to supply the transmitting coil with testing clock pulses. Transistor transmitters have relatively low internal resistances. To match the transmitting coil to the transistor transmitter, several windings are formed connected in parallel to the output of the pulse generator.

It is favourable for increasing the efficiency of the conversion of acoustic to electrical energy if the receiving coil too has a large number of turns. A limit for the number of turns is the cut-off frequency, dependent on the capacity of the winding. The number of windings chosen is preferably high enough for the cut-off frequency determined by the winding capacity to be close to the working frequency of the electro-acoustic transducer 7. The cable capacity of the power lines must also be added to the winding capacity and taken into account.

The working frequency of the electro-dynamic transducer 7 is determined by the type of wave to be generated and by the spatial periodicity of the coil winding. Since in the Rayleigh wave and the shear wave irradiated in a grazing manner the wavelength $\lambda_s$ matches the period of the winding of transmitting coil 12, the following relationships apply for the working frequencies:

$$f = C_R / \lambda_s$$

or $$f = C_t / \lambda_s,$$

with $C_R$ being the propagation velocity of the Rayleigh wave and $C_t$ the transversal wave velocity. For steels, the following relationship applies between the quantities $C_R$ and $C_t$:

$$C_R = 0.9 \times C_t$$

Figure 6:
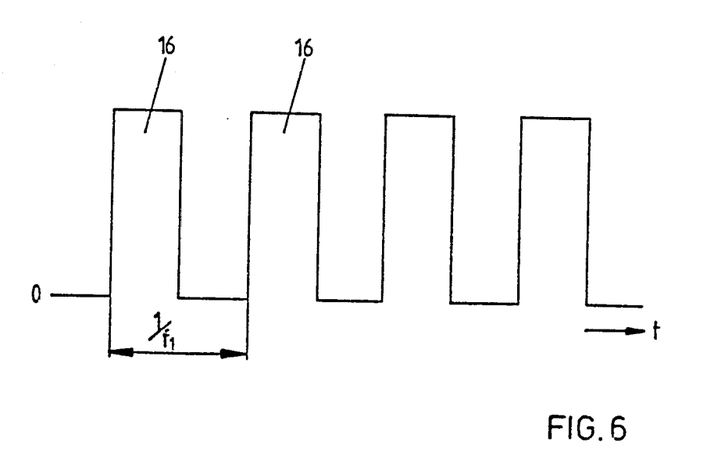
FIG. 6 is a diagram of the timing of testing clock pulses.

In order that all ultrasonic waves excited by the individual line elements of the meander-type transmitting coil 12 and of the transducer 7 can interfere with one another, the duration of excitation must be selected sufficiently large. The number of individual pulses (burst) 16 of a pulse group with which the transmitting coil 12 is triggered in pulse-echo mode depends on the number of meander elements in transmitting coil 12. It is best for the number of single pulses 16, shown in FIG. 6 as a function of time t, to correspond to the number of line elements 17 of the meander-type transmitting coil 12. This has the advantage that the pulse group passing through the electro-acoustic transducer 7 reaches each line element 17 with a phase shift by which an increased radiation of the ultrasonic waves is achieved. As shown in FIG. 6, the period of a single pulse here is in inverse proportion to the working frequency f.

The maximum relative bandwidth of the ultrasonic signals so excited is $B - _{6dB} = 100\% (N/2)$ with N being the number of line elements 17.

The Rayleigh wave has a depth of penetration of about twice the wavelength and is concentrated on the areas directly underneath the surface. Using this wave, saw cuts whose depth is less than 10% of the wavelength can be evidenced, with the possibility of determining the wavelength using the periodicity of the winding. It must be noted that the error amplitude is not monotonically linked with the crack depth.

In the case of the shear wave with grazing incidence, a substantially larger zone in the area close to the surface can be tested, and here the error amplitude is monotonically linked with the crack depth.

An electro-acoustic transducer 7 of the above design radiates with equal intensity in both directions. One possibility for improving the directional characteristic is to interlace a second meander-wound transmitting coil with the first one 12 and to control the second coil with a 90° phase difference. When the pulse duration of the transmitted signal is brief, the radiated ultrasonic signals can then only interfere with one another in the positive direction.

FIG. 1 shows magnetic field lines 18 following the curve in the outer wall of pipe 1, and magnetic field lines 19 which enter the surface of pipe 1 at an angle at that point at which the electro-dynamic transducer is located. The transducer 7 generates a Rayleigh wave whose direction is numbered 20 in FIG. 1, and a shear wave running in the longitudinal direction of the pipe. The Rayleigh wave is used to pick up longitudinal faults in pipe 1. A longitudinal error is numbered 21 in FIG. 1 and represented by a line from the surface of pipe 1 projecting some way into the pipe wall.

Figure 7:
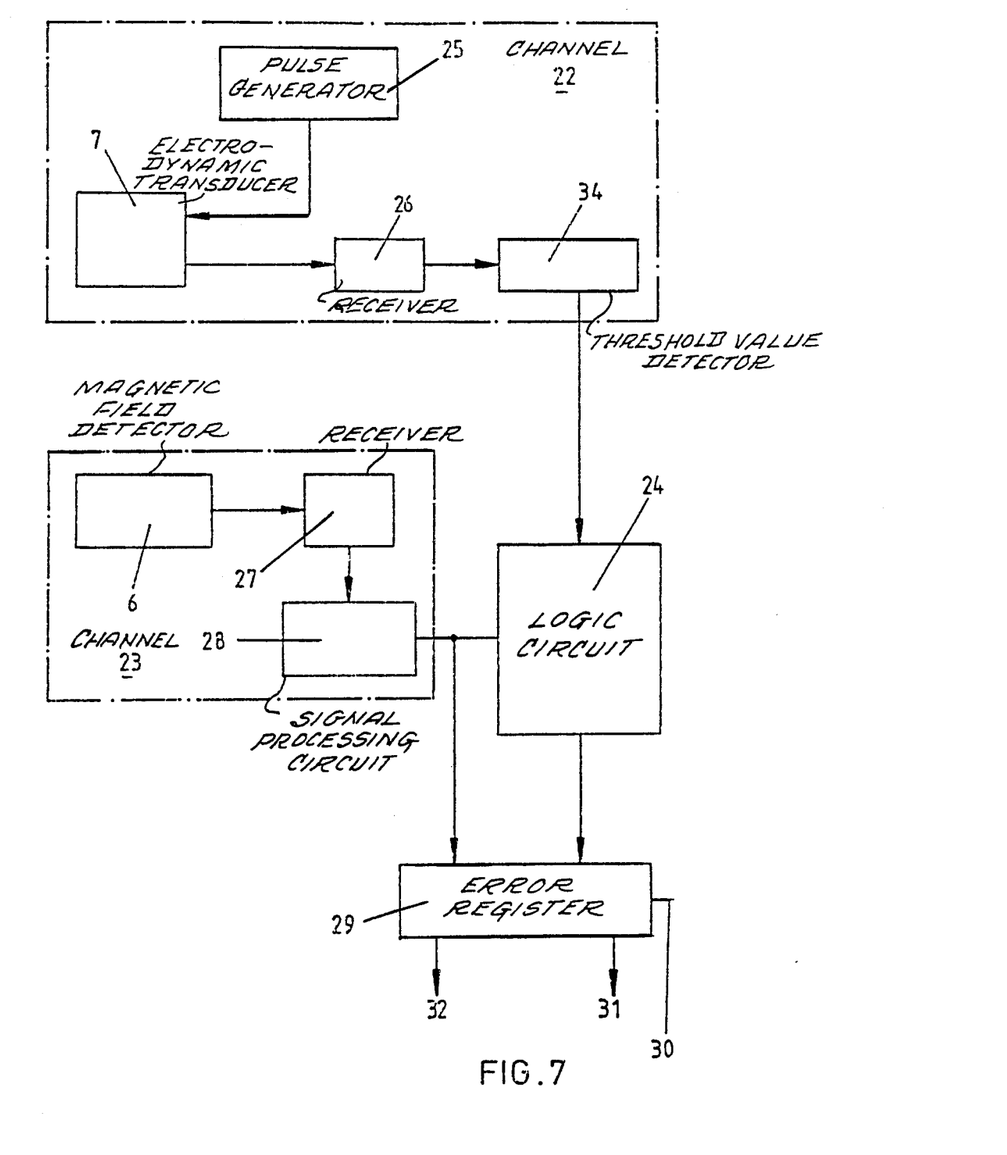
FIG. 7 is a block diagram of an arrangement for determining the nature of structural faults in the bodies to be tested.

Referring to FIG. 7, an arrangement for determining the nature of structural faults in pipe 1 comprises 2 channels 22, 23, linked to a logic circuit 24. Surface waves are generated with channel 22 and errors in pipe 1 detected on the basis of the values received. Channel 22 contains the electrodynamic transducer 7, whose transmitting coil 12 is connected to a testing pulse generator 25. Receiving coil 13 of transducer 7 is connected to a receiver 26, which may be an amplifier. A threshold value detector 34 is connected to receiver 26, threshold value of said detector being settable to selected values.

Channel 23 contains the magnetic field detector 6 whose output is connected to a receiver 27, e.g. an amplifier. Receiver 27 feeds a signal processing circuit 28 in which the measured leakage flux signals are processed by comparing them with specified threshold values, for example. Standard components can be used for evaluation of the measurement signals of the ultrasonic and leakage flux signals, i.e. the two channels 22, 23 can be built up of commercially available components.

The outputs of threshold value detector 34 and signal processor 28 are connected to the logic circuit 24. Signal processing circuit 28 is at the same time connected to an error register 29 which is further connected to the output of logic circuit 24, which carries out an AND operation with the output signals generated by threshold value detector 34 and signal processing circuit 28. An input 30 of error register 29 is supplied with the test clock pulses.

The test pulse generator 25 feeds pulses into the electrodynamic transducer 7. The signals picked up by the receiving coil are amplified in receiver 26. The threshold value detector 34 reduces the signals resulting from the test to values which only occur in the case of faults. These values pass to the logic circuit.

The values measured by magnetic field detector 6 pass via receiver 27, which amplifies them, to the signal processing circuit 28, which only transmits to the logic circuit 24 and to the error register 29 those data which have been assigned to faults in pipe 1.

If in channel 22 a threshold value is exceeded and the same is detected in channel 23 at the same time, the fault is external. The logic circuit 24 carries out an AND operation and feeds an appropriate signal into the error register 29. Errors only picked up by channel 23 also pass into error register 29 which has outputs 31 and 32 which show whether the fault detected is external or internal, respectively. Since there can be time differences between fault signals and their classification, all findings are buffered in the error register 29 synchronous to the testing clock pulse and therefore stored depending on the location of the test. This allows the fault to be precisely located.

The signal processing circuit 28 can evaluate the size and/or form of the fault signals and supply an analog value which is the dimension for the fault depth.

Referring to FIG. 1, an electro-dynamic transducer 33 is provided in pole 5, said transducer generating ultrasonic waves with which the wall thickness of pipe 1 is measured.

Pipe 1 has for instance a diameter of R. If the central axes 42, 43 through magnetic field detector 6 and transducer 7 enclose an angle of $\beta$ in the centre point of pipe 1, magnetic field detector 6 and transducer 7 are separated at the circumference of pipe 1 by the arc a $=2 \times R \times 2/360°$, which is known. With magnetic field detector 6, a fault in the rotary direction numbered 44 in FIG. 1 is first picked up. The respective rotational position of the detected fault is determined using a resolver. With constant revolving time, the respective position of the fault picked up by magnetic field detector 6 in relation to transducer 7 can also be calculated. The longitudinal position of the fault is determined on the basis of the speed and the feed velocity.

Using wave velocity $C_R$, the relative velocity between transducer 7 and pipe 1, and the arc distance a, the delay for an anticipated fault echo can be determined when an error is picked up by magnetic field detector 6. A time window is set in the logic circuit 24 based on the delay. If the value determined with threshold value detector 34 exceeds the set threshold within the time window, the leakage flux measurement and the surface wave measurement indicate the fault, i.e. the fault extends up to the surface. If the threshold value detector 34 does not detect an overrun of the threshold value, the fault is internal. The pulse frequency of transducer 7 must be synchronized with the speed of pipe 1.

A time window is generated in similar manner for shear waves, said window depending on the distance between magnetic field detector and transducer projected onto the circumference of pipe 1, on the relative velocity between transducer and pipe, and on the wave velocity of the shear waves.

I claim:

1. A method of selectively, non-destructively testing ferromagnetic bodies for structural anomalies during a relative motion between a measuring apparatus and a respective body, in which at least one magnetic field is generated causing leakage flux in case of structural anomalies, which flux is measured by at least one magnetic field detector, and ultrasonic waves are generated making use of the magnetic field in conjunction with at least one electro-dynamic transducer, these ultrasonic waves being reflected from structural anomalies and measured by said at least one electro-dynamic transducer, characterized by the following steps, (a) generating the ultrasonic waves as surface waves, detecting structural anomalies reaching the surface of the respective body from the measured reflected waves;
    (b) distinguishing structural anomalies reaching the surface at one point on said body from structural anomalies not reaching the surface, by detecting whether both the leakage flux measurement and the surface wave measurement are indicating structural anomalies at said point, or whether the leakage flux measurement only is indicating structural anomalies, indications of structural anomalies by both measurements signifying that a structural anomaly reaching the surface exists, and
    (c) upon determining that a structural anomaly reaching the surface of the body exists, determining the depth of impression of the structural anomaly from the size and/or the form of the leakage flux measured value at said point.

2. A method according to claim 1, characterized in that, in the case of oblong bodies, Raleigh waves are generated for detecting structural anomalies, which waves extend in the longitudinal direction of the body up to its surface, and further characterized in that glancingly acoustic-irradiated shearing waves are generated for detecting structural anomalies extending in the transverse direction of the body up to its surface.

3. An apparatus for the non-destructive testing of ferro-magnetic bodies for structural anomalies during a relative motion between a measuring device and the respective body, in which, on the one hand, at least one magnetic field is generated causing leakage flux in case of structural anomalies, which flux is measured by at least one magnetic field detector, and, on the other hand, ultrasonic waves are generated, making use of the magnetic field, by means of at least one electro-dynamic transducer, these ultrasonic waves being reflected from structural anomalies and measured by said at least one electrodynamic transducer, characterized by the following features (a) for generating the magnetic field, at least two magnets, with their pole shoes at a distance from each other, are pointed at the surface of the body to be tested;
    (b) a magnetic field detector is arranged in the space between the pole shoes close to the surface of the body;
    (c) at a place close to the surface of the body, where the magnetic field has field components both perpendicular to the surface and extending in the direction of the surface and parallel thereto, there is arranged the electro-dynamic transducer having a transmitting coil;
    (d) the electro-dynamic transducer including a receiving coil which is connected to a first input of an interconnection logic via a threshold value detector, the magnetic field detector being connected to the input of a computerized signal processing circuit, the output of which is connected to a second input of the interconnection logic circuit, and
    (e) the output of said interconnection logic being connected to a first input of a defect register, a second input of said defect register being connected to the output of said signal processing circuit such that a value from the interconnection logic or the computerized signal processing circuit can be read in said defect register in synchronism with test timing pulses generated in the transmitting coil of the electro-dynamic transducer, the output of said interconnection logic providing an indication of whether an anomaly is an internal or an external anomaly, and the output of said signal processing circuit providing an indication of the depth of said anomaly 4. Device according to claim 3, characterized in that the electro-dynamic transducer (7) is arranged close to a magnetic pole (4).

5. Device according to claim 3 characterized in that the electro-dynamic transducer (7) has a meander-wound transmitting coil (12) whose turns are arranged in grooves (14) of a spool (15) arranged at a constant distance from the surface of body (1).

6. Device according to claim 5, characterized in that the periodicity of the winding of the transmitting and the receiving coils (12, 13) respectively is equal to the wavelength ($\lambda_s$) of the ultrasonic waves generated.

7. Device according to claim 3, characterized in that the receiving coil (13) is meander-wound and arranged interlaced with the transmitting coil (12) in the grooves (14) of the spool (15).

8. Device according to claim 3, characterized in that the transmitting coil (12) can be subjected to pulses (16) whose number corresponds to the number of line elements (17) of the meander-type winding.

9. Device according to claim 3, characterized in that the line elements of a further transmitting coil are arranged between the line elements (17) of the transmitting coil spaced a quarter-period of the wavelength ($\lambda_s$), said further coil being supplied with pulses phase-shifted by 90° against the pulses of the first transmitting coil (12).

10. Device according to claim 3, characterized in that a series of capacitance is connected to the transmitting coil (12) or a parallel capacitance to the receiving coil, and that the arrangement comprising the transmitting coil (12) and the series capacitance, or the receiving coil (13) and the parallel capacitance, is designed as a resonant circuit.

11. Device according to claim 3, characterized in that the transmitting coil (12) is provided with numerous turns connected by groups in parallel with a testing pulse generator (25) designed as a transistor transmitter.

12. Device according to claim 3, characterized in that the number of turns of the receiving coil (13) is matched to the winding capacity such that the winding capacity determines a cut-off frequency which is slightly larger than the frequency of the pulse group or the sequential frequency of the pulse group for testing.

13. Device according to claim 3, characterized in that the magnets (2, 3), the magnetic field detector (6), and the transmitting and receiving coils (12, 13) together with a spool (15) are arranged stationary, while the body (1) to be tested carries out a rotary movement and a longitudinal shift.

14. Device according to claim 3 characterized in that the magnets, the magnetic field detector, and the transmitting and receiving coils are arranged rotatably about the longitudinal axis (37) of the body to be tested, while the body to be tested can be shifted in its longitudinal axis during testing.

15. Device according to claim 3, characterized in that the magnets, the magnetic field detector, and the transmitting and receiving coils are arranged rotatably about the longitudinal axis of the body to be tested and displacably in the direction of the longitudinal axis (37), and that the respective body is arranged stationary during testing.

16. Device according to claim 3, characterized in that after detection of a fault using the magnetic field detector (6), a time window for the duration of the pulse echo of the surface waves in relation to the fault is determined, said time window being dependent on distance between the magnetic field detector (6) and the transducer (7) projected onto the surface of the body (1), on the relative velocity of the body (1) against the magnetic field detector (6) and the transducer (7), and on the wave velocity of the surface waves, and that the fault is external if the threshold value overrun detected by the threshold value detector (34) is within the time window.

17. Device according to claim 3, characterized in that the speed of body (1) is synchronized with the pulse frequency of the pulses for the transducer (7).

* * * * *